United States Patent [19]

Regan

[11] Patent Number: 4,574,813

[45] Date of Patent: Mar. 11, 1986

[54] PACE PULSE SIGNAL CONDITIONING CIRCUIT

[75] Inventor: Richard J. Regan, Beverly, Mass.

[73] Assignee: Hewlett-Packard Company, Palo Alto, Calif.

[21] Appl. No.: 551,628

[22] Filed: Nov. 14, 1983

[51] Int. Cl.[4] .............................................. A61B 5/04
[52] U.S. Cl. .............................. 128/697; 128/419 PT
[58] Field of Search ................... 128/419 PT, 696, 697

[56] References Cited

U.S. PATENT DOCUMENTS

| | | | |
|---|---|---|---|
| 3,897,774 | 8/1975 | Burdick et al. | 128/419 PT |
| 3,986,496 | 10/1976 | Brastad | 128/419 PT |
| 4,105,023 | 8/1978 | Marchese et al. | 128/419 PT |
| 4,149,527 | 4/1979 | Naylor et al. | 128/697 |
| 4,226,245 | 10/1980 | Bennett, Jr. | 128/419 PT |
| 4,243,045 | 1/1981 | Maas | 128/419 PT |

Primary Examiner—William E. Kamm
Attorney, Agent, or Firm—Donald N. Timbie

[57] ABSTRACT

An EKG signal processing apparatus comprising an input to which the EKG signal may be applied, an output at which the processed EKG signal is to appear, a resistor and a normally conductive signal switch connected in series between one terminal of said input and one terminal of said output, a capacitor connected across the output, a differentiator, and a bipolar comparator for providing a signal indicating the presence of a pace pulse at said input, and a signal switch control responsive to said signal for making said signal switch nonconductive for at least a portion of a pace pulse and until any voltage following the pace pulse has reached a low value.

15 Claims, 49 Drawing Figures

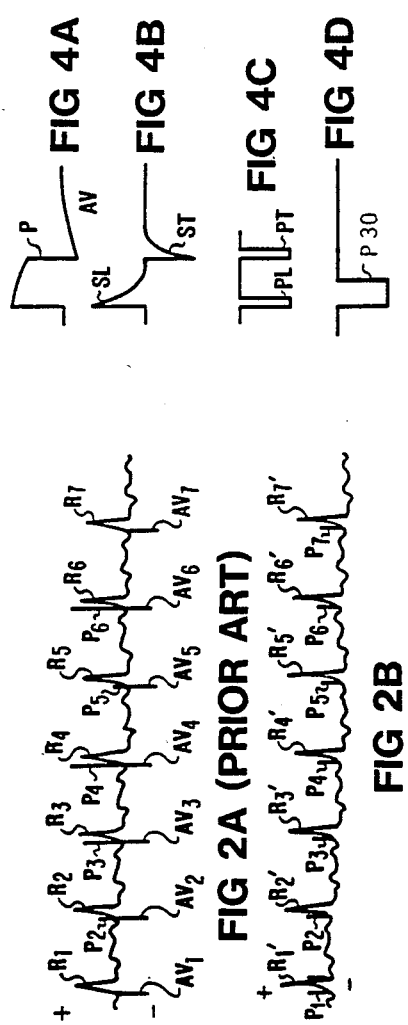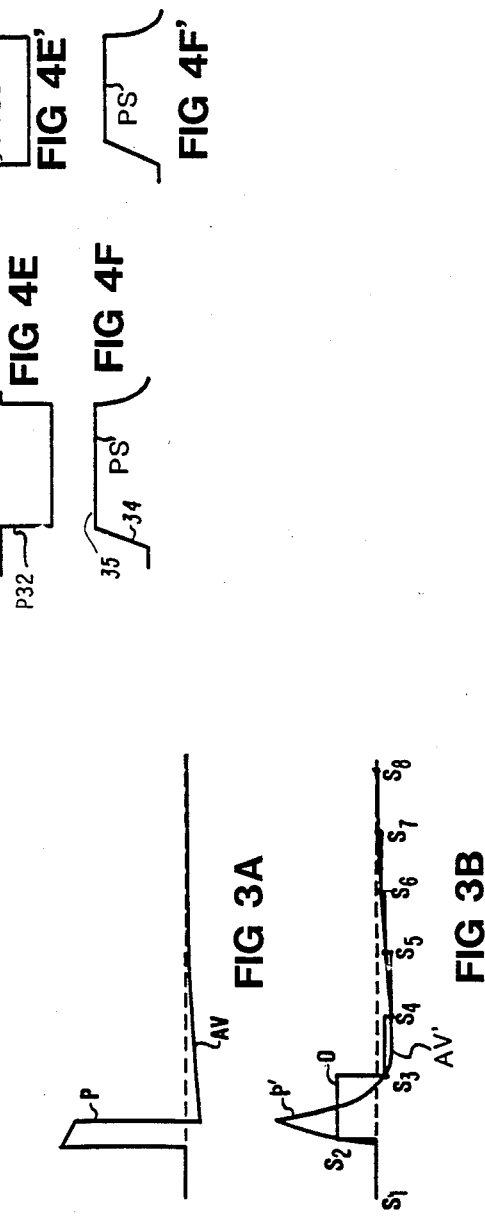

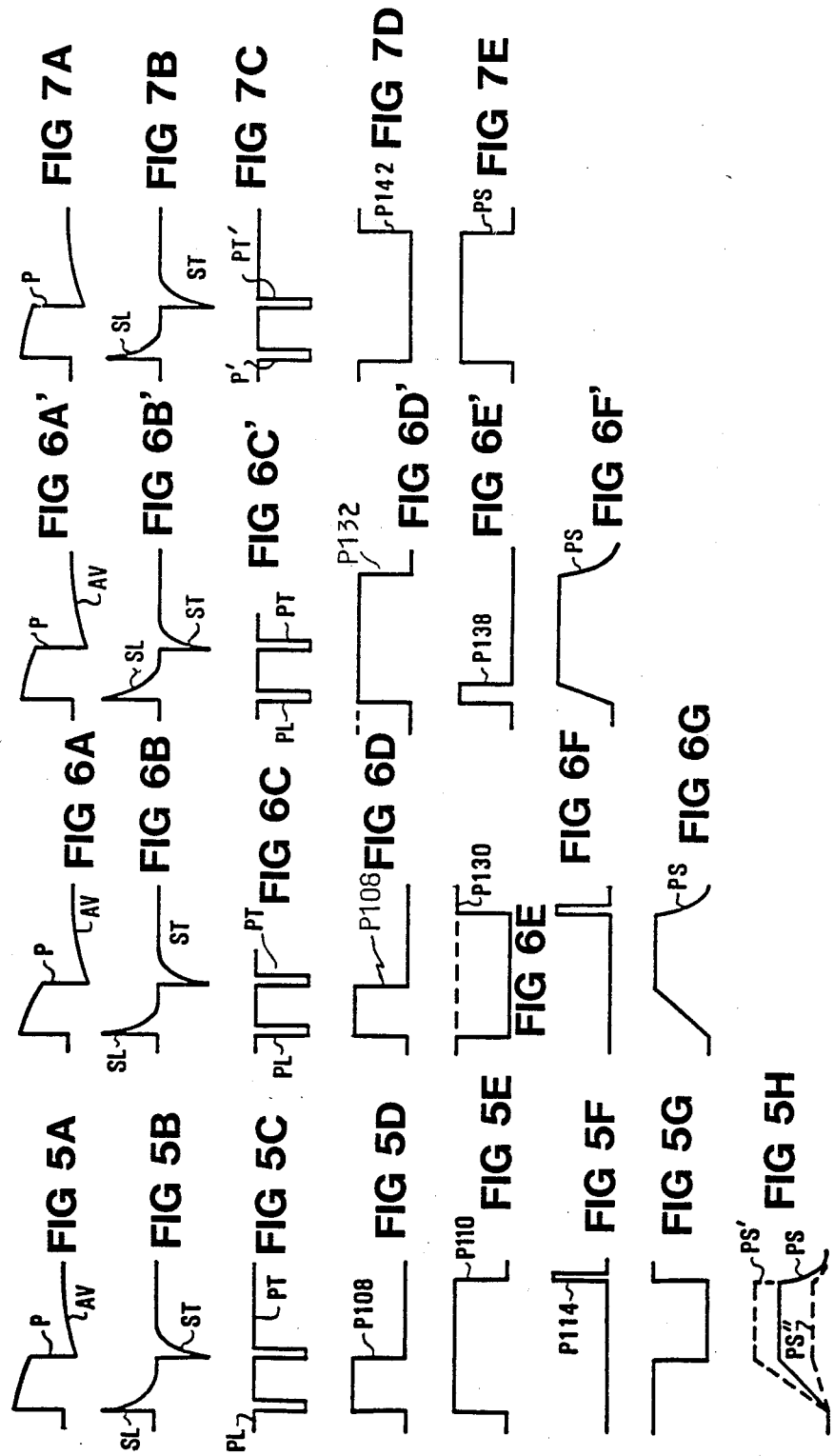

PACE PULSE SIGNAL CONDITIONING CIRCUIT

BACKGROUND OF THE INVENTION

When a patient has a pacemaker, the electrical pulses it provides are added to the EKG waves derived from that patient by the electrodes of an electrocardiograph. Depending on the pacemaker employed and its adjustment, the duration of the pace pulses may be from about 100 to about 2000 microseconds, and their amplitude at most electrode locations usually exceeds that of the EKG wave by a substantial amount. Pacemakers in which the pace pulses are capacitively coupled to the patient cause a voltage of the opposite polarity that can last for as long as several milliseconds following the pace pulse. Hereinafter, this voltage will be referred to as the after-voltage.

A conventional electrocardiograph displays a single EKG wave, but electrocardiographs have recently become available that display a plurality of EKG waves at the same time by rapidly sampling each wave in sequence and using the samples derived from each wave to reproduce it. Thus, the voltages derived from different electrodes on the patient's body can be simultaneously displayed. Due to limitations in slew rate and frequency response, conventional electrocardiographs may be disturbed by the high amplitude of a pace pulse so as to display it with an incorrect amplitude, and both types of electrocardiographs can respond to the after-voltage so as to display a pulse of the wrong polarity. Electrocardiographs utilizing sampling techniques display representations of the pace pulses that vary in amplitude depending on the phase relationship between the sampling times and the pace pulses, and no pace pulses will be displayed if no portion of a pace pulse occurs during a sample.

BRIEF SUMMARY OF THE INVENTION

In accordance with this invention, a pulse PS is substituted for the pace pulse P and any after-voltage that may be present is prevented from reaching the output. The substitute pulse PS may be derived in a number of ways:

(1) by integrating a portion of the pace pulse P so that PS is proportional to the amplitude of the pace pulse P;

(2) by integrating the entire pace pulse P so that $P_S$ is proportional to the product of the amplitude and duration of the pace pulse P;

(3) by integrating current from a constant current source so that PS has an amplitude that is not related to the amplitude of P but is related to its duration; and (4) by generating PS in such manner that it is not related to any parameter of the pace pulse P.

In some EKG systems, as many as twelve or more pairs of leads are provided, each with a different EKG signal, and although the pace pulses are weak or nonexistent in some of the signals, it is desirable that they be appropriately displayed. In order to do this, processing circuits constructed in accordance with this invention are respectively connected to two or three leads, one or more of which are likely to have pace pulses of significant amplitude, and normally closed signal switches are respectively connected in each of the other leads. These switches are controlled by the signals used in one or more of the invented circuits to control their own signal switches. This is less expensive than providing a separate invented circuit for each lead.

BRIEF DESCRIPTION OF THE DRAWINGS

FIG. 2A is an electrocardiogram produced by a system of FIG. 1 that uses coupling circuits of the prior art;

FIG. 2B is an electrocardiogram produced by a system of FIG. 1 that uses the coupling circuits of the invention;

FIG. 3A illustrates a pace pulse and the after-voltage that follows it when it is capacity-coupled;

FIG. 3B illustrates the effect of filtering and sampling a wave such as shown in FIG. 3A;

FIGS. 4A, 4B, and 4C are waveforms appearing at like-lettered points in FIGS. 4 and 4';

FIGS. 4D, 4E, and 4F are waveforms appearing at like-lettered points in FIG. 4;

FIG. 4' is a block diagram of a second embodiment of the preferred specie of an EKG processing circuit of this invention in which the amplitude of the substitute pulse PS is different from that in FIG. 4;

FIGS. 4'D, 4'E, and 4'F are waveforms appearing at like-lettered points in FIG. 4';

FIGS. 5A, 5B, 5C, 5D, 5E, 5F, 5G and 5H are waveforms appearing at like-lettered points in FIGS. 5 and 5';

FIG. 5' is a block diagram of a second embodiment of the second specie of an EKG processing circuit of this invention in which the amplitude of the substitute pulse PS is different from that in FIG. 5;

FIGS. 6A, 6B, 6C, 6D, 6E, 6F and 6G are waveforms appearing at like-lettered points in FIG. 6;

FIG. 6' is a second embodiment of the third specie of an EKG processing circuit of this invention in which the substitute pulse PS has a constant amplitude;

FIGS. 6A' through 6F' are waves that appear at like-lettered points in FIG. 6';

FIGS. 7A through 7E are waves that appear at like-lettered points in FIG. 7.

DETAILED DESCRIPTION OF THE INVENTION

Figure 1:
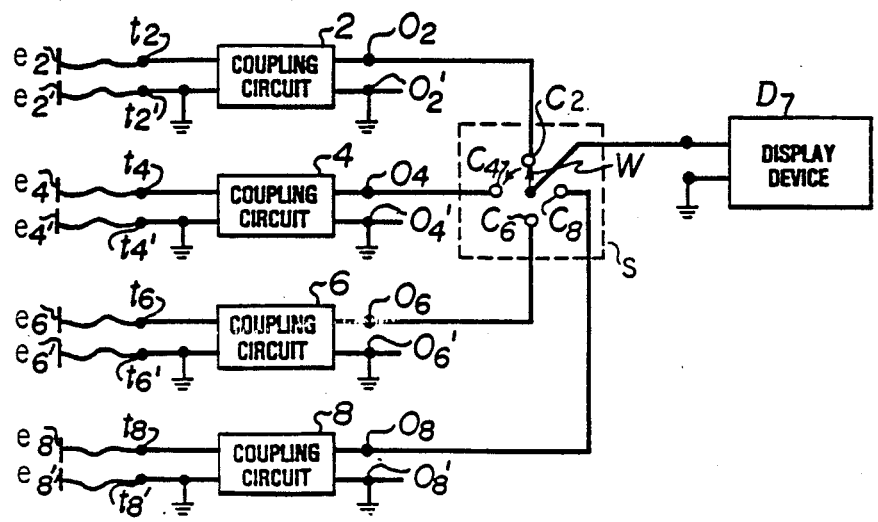
FIG. 1 illustrates an electrocardiographic system employing sampling so that four EKG signals may be displayed at the same time.

The electrocardiographic system schematically illustrated in FIG. 1 has four sets of electrodes $e_2, e_2'; e_4, e_4'; e_6, e_6'$ and $e_8, e_8'$ that are respectively connected to the input terminals $t_2, t_2'; t_4, t_4'; t_6, t_6'$ and $t_8, t_8'$ of coupling circuits 2, 4, 6 and 8. The input terminals $t_2', t_4', t_6'$ and $t_8'$ are connected to a point of reference potential which may be floating ground. The output terminals of the coupling circuits 2, 4, 6 and 8 are $o_2, o_2'; o_4, o_4'; o_6, o_6'$ and $o_8, o_8'$ respectively, and output terminals $o_2', o_4', o_6'$ and $o_8'$ are connected to points of the reference potential just mentioned. The output terminals $o_2, o_4, o_6$ and $o_8$ are respectively connected to the contacts $c_2, c_4, c_6$ and $c_8$ of an electronic sampling switch S having a commutating contact W which is connected to the input of a display means D that respectively produces separate waves with the samples from the contacts $c_2, c_4, c_6$ and $c_8$ in a manner known to those skilled in the art.

With the coupling circuits 2, 4, 6 and 8 of FIG. 1 constructed in accordance with the prior art so as to have 100 Hz low pass filters, EKG waves produced by the display means D appeared as illustrated in FIG. 2A, in which the R waves $R_2$ through $R_6$ have positive pace pulses $P_2$ through $P_6$ respectively occurring prior to them that vary in amplitude and, as noted in connection with the R waves $R_1$ and $R_7$, the pace pulses can even be entirely missing. The reason for this can be understood from the following. If a rectangular pace pulse is AC-coupled to the patient's body, it will appear as a pulse P, illustrated in FIG. 3A, followed by an after-voltage AV of the opposite polarity. The pulse P is the only effective part of the wave of FIG. 3A and will be referred to herein as a pace pulse. After passing through a 100-cycle low pass filter in the usual coupling circuit of FIG. 1, the pace pulse P and its after-voltage AV appear as respectively indicated at P' and AV' of FIG. 3B. Now if it is sampled at points $s_1$ through $s_8$ and applied to a sample-and-hold circuit, it will appear as indicated by the stepped wave O of FIG. 3B. The representation of the pace pulse P' in the wave O has a smaller amplitude than if a sample occurred at the peak of the filtered pulse P'; and if no sample occurs within the pace pulse P', its representation will be zero as in connection with R waves $R_1$ and $R_7$ of FIG. 2A. In a system using sampling, this latter phenomenon will happen regardless of whether the pacemaker is directly coupled or capacitively coupled.

It is also to be noted that the EKG waveforms of FIG. 2A produced by the prior art contain negative pulses $AV_1$ through $AV_7$ that extend in a negative direction. They are caused by the negative after-voltage AV, such as shown in FIG. 3A, which occurs when the pacemaker is capacitively coupled. Because of the duration of the after-voltage AV, a plurality of samples $s_3$ through $s_8$ occur during its filtered form AV' shown in FIG. 3B. They appear as being widely separated in FIG. 3B due to its expanded time scale but appear as a single pulse such as any one of $AV_1$ through $AV_7$ in the much-reduced time scale of the display. The amplitude of the negative pulses $AV_1$ through $AV_7$ is more nearly uniform than that of the pace pulses $P_2$ through $P_6$ because the after-voltage AV' is so broad that at least one of the samples occurs near its peak.

The EKG waves that were applied to the coupling circuits of FIG. 1 in producing the display of FIG. 2A were recorded and then applied to a processing circuit constructed in accordance with this invention. The display then appeared as in FIG. 2B. Note that all pace pulses are represented, that all have the same amplitude, and that no negative pulses such as $AV_1$ through $AV_7$ are present.

PREFERRED SPECIE OF THE INVENTION

Figure 4:
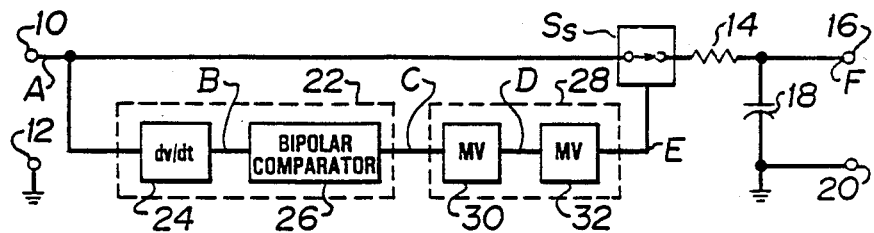
FIG. 4 is a block diagram of one embodiment of a preferred specie of an EKG processing circuit of this invention in which the voltage produced in response to pace pulses is proportional to their amplitude.
Figure 4:
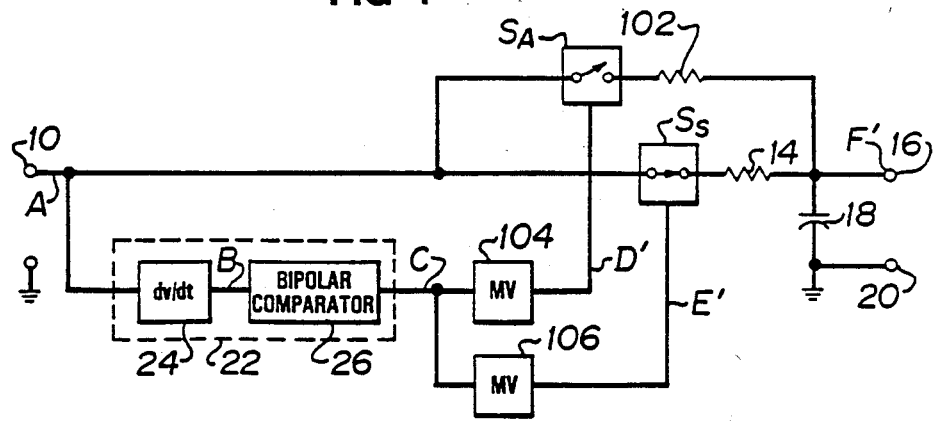

A block diagram of a first embodiment of a preferred specie of this invention that was actually used in obtaining the processed EKG signals of FIG. 2B is shown in FIG. 4. The voltage waves of FIGS. 4A through 4F that are used in explaining its operation appear at correspondingly lettered points. This circuit derives the substitute pulse PS by integrating a portion of a pace pulse P so that the substitute pulse PS has an amplitude proportional to the amplitude of a pace pulse.

The EKG signals to be processed are applied across input terminals 10 and 12, the latter being connected to a point of reference potential such as floating ground. A normally closed signal switch $S_s$ and a resistor 14 are connected in series in either order between the input terminal 10 and an output terminal 16, and a capacitor 18 is DC-coupled between the output terminal 16 and an output terminal 20 that is connected to the point of reference potential. As in the prior art, the values of the resistor 14 and the capacitor 18 are such as to form a low pass filter having a cut-off just above the highest frequency of interest in the EKG signals, e.g., 100 cycles, so as to reject high frequency noise.

When a positive pace pulse P of FIG. 4A arrives at the input 10, 12, its presence is detected by a pace pulse sensing means 22 coupled thereto that is comprised of a differentiation circuit 24 and a bipolar comparator 26. As shown in FIG. 4B, the differentiation circuit 24 outputs a positive signal SL coincident with the leading edge of the pace pulse P and a negative signal ST coincident with the trailing edge of the pace pulse P. The bipolar comparator 26 produces pulses PL and PT of FIG. 4C that are respectively coincident with the leading and trailing edges of the pace pulse P and are negative regardless of its polarity.

A signal switch control means 28 is herein shown as being comprised of a 50-microsecond monostable multivibrator 30 that is triggered by the negative-going edge of the pulse PL so as to produce a negative pulse P30 (FIG. 4D) and a 10-millisecond monostable multivibrator 32 that is triggered by the positive-going edge of a pulse P30 so as to produce at its output a pulse P32 (FIG. 4E). When P32 is low, it keeps the normally closed switch $S_s$ open so that the period during which the signal switch $S_s$ is made nonconductive starts during the pace pulse P.

Thus, the pace pulse P is integrated by the resistor 14 and the capacitor 18 only during the pulse P30 of FIG. 4D, which was 50 microseconds in the tests producing the wave of FIG. 2B, so as to produce an increasing voltage across the capacitor 18 as indicated by the sloping line 34 of FIG. 4F. At the end of the pulse P30 of FIG. 4F, the integrated voltage across the capacitor 18 reaches a maximum value indicated at 35 that is proportional to the amplitude of the pace pulse P. The maximum value lasts as long as the switch $S_s$ is open, i.e., for a period equal to the duration of the pulse P32. At the end of the pulse P32, the switch $S_s$ closes and the voltage across the capacitor 18 assumes the value of the voltage at the input 10, 12. The actions just described form the pulse PS of FIG. 4F that is substituted for the pace pulse P.

The duration of the pulse P32 and therefore the time after the pace pulse P during which the switch $S_s$ is nonconductive is such that the after-voltage AV will have a negligible effect on the integrated voltage produced across the capacitor 18. This depends, of course, on the duration and amplitude of the after-voltage AV, which can vary, but with present pacemakers a period of approximately 10 milliseconds has been found to be satisfactory.

Figure 4G:
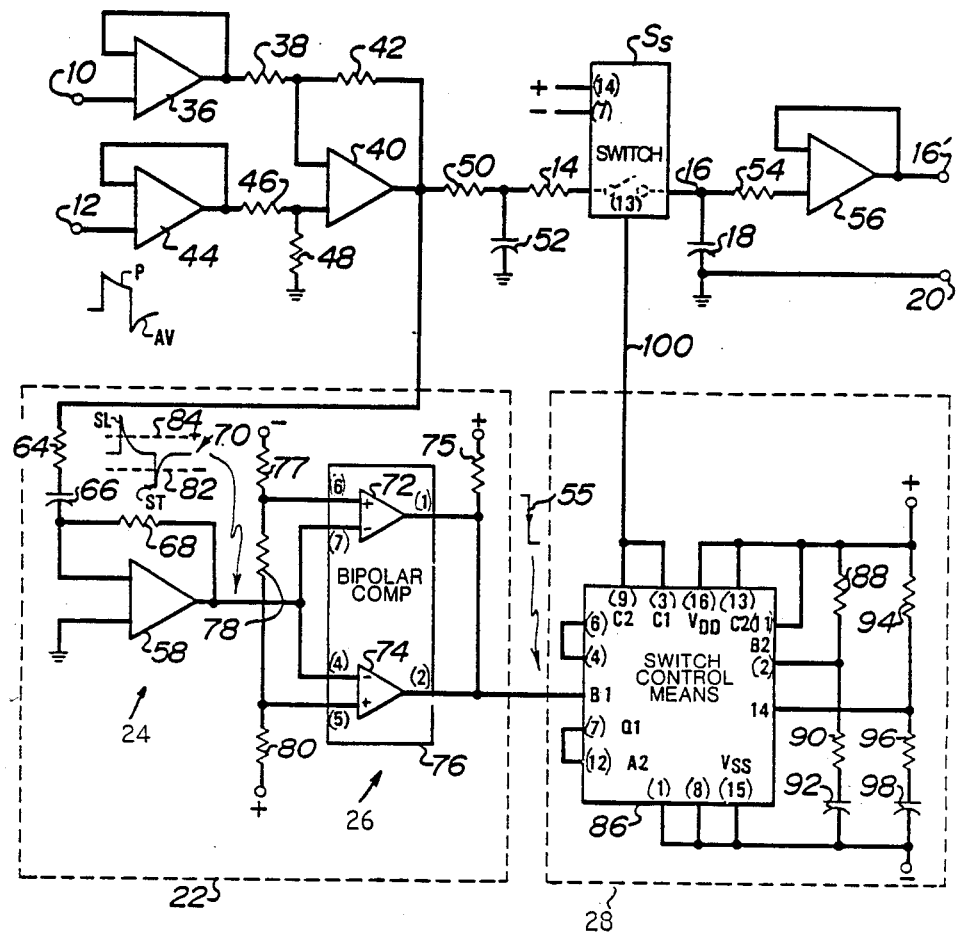
FIG. 4G is a schematic diagram of a circuit for FIG. 4.

Reference is now made to FIG. 4G which schematically illustrates one form of circuit that may be used to carry out the functions just described in connection with the block diagram of FIG. 4. Components corresponding to those of FIG. 4 are designated in the same way, and the designations inside the solid-line rectangles indicate the particular terminals of the solid state devices.

The input terminal 10 is coupled via a buffer amplifier 36 and a resistor 38 to one input of a differential amplifier 40, and a resistor 42 is connected between that input of the amplifier 40 and its output. The input terminal 12 is connected via a buffer amplifier 44 and a resistor 46 to the other input of the differential amplifier 40, and a resistor 48 is connected between that input of the amplifier 40 and a point of reference potential. A resistor 50 and a capacitor 52 that are connected in series from the output of the amplifier 40 to a point of reference potential form an additional low pas filter, not shown in FIG. 4, that has no effect on the EKG signal but allows some latitude of adjustment of the narrow pace pulse to establish an exact scale factor or proportionality factor of the substitute pulse PS with respect to the actual pace pulse amplitude. The junction of the resistor 50 and the capacitor 52 is connected by the resistor 14 to the input of the signal switch $S_s$, herein shown as being a solid state device No. 4066, and the output of the switch $S_s$ is connected to a point of reference potential by the capacitor 18 across which the substitute pulse PS indicated in FIG. 4F appears. As in FIG. 4, the output terminal 20 is connected to the side of the capacitor 18 that is connected to reference potential, and the other output terminal 16 is at the other side of the capacitor 18. In order to prevent subsequent devices from placing an impedance in shunt with the capacitor 18 that could interfere with the operation of the circuit, the output terminal 16 is connected via a protection resistor 54 and a buffer ampifier 56 to another output terminal 16'.

The control of the switch $S_s$ as described in connection with FIG. 4 is attained by the following circuit elements of FIG. 4G. The differentiator 24 is comprised of a resistor 64 and a capacitor 66 connected in series in the order named between the output of the amplifier 40 and one input of a differential amplifier 58, and the other input of the amplifier 58 is connected to a point of reference potential. A resistor 68 is connected between the output of the amplifier 58 and the input that is connected to the capacitor 66. As is well understood by those skilled in the art, the amplifier circuit just described will differentiate the pace pulse P appearing at the output of the amplifier 40 so as to produce at its output a wave 70 having the first pulse SL of FIG. 4B coincident with the leading edge of the pace pulse P and of the same polarity with respect to the reference potential, and a second pulse ST of FIG. 4B coincident with the trailing edge of the pace pulse P and of the opposite polarity.

The output of the differentiating amplifier 58 is connected to the bipolar comparator 26 by a connection to the inverting inputs of differential amplifiers 72 and 74 contained within a chip 76, herein indicated as being No. LM-339. The outputs of the amplifiers are connected to a point of potential that is positive with respect to the reference potential via an output resistor 75. Resistors 77, 78 and 80 are connected in series in the order named between a point of voltage that is negative with respect to the reference potential and a point of voltage that is positive thereto. The values of the resistors 77, 78 and 80 are so chosen that the junction of the resistors 77 and 78, which is connected to the noninverting input of the amplifier 72, is negative with respect to the reference potential, as indicated by a dashed line 82 shown with the wave 70; and the junction of the resistors 78 and 80, which is connected to the noninverting input of the amplifier 74, is positive with respect to the reference potential, as indicated by the dashed line 84 shown with the wave 70.

The operation of the chip 76 and its associated circuit as a bipolar comparator is as follows. When the positive pulse SL at the output of the differential amplifier 58 becomes more positive than the voltage indicated by the dashed line 84, the output of the differential amplifier 72 goes negative as indicated by the negative-going output signal 55. Should the polarity of the pace pulse P be negative instead of positive, as shown, the pulse SL occurring at its leading edge will be negative. When it becomes more negative than the voltage indicated by the dashed line 82, the output of the amplifier 72 goes negative as indicated at 55. In this particular embodiment of the invention, no use is made of the pulse ST formed by the differential amplifier 58.

The functions of the switch control means 28 of FIG. 4 are carried out by a chip 86, type No. 4538. Its negative-triggered input terminal B1 is connected to the outputs of the amplifiers 72 and 74, and it includes within it two monostable multivibrators corresponding to the multivibrators 30 and 32 of FIG. 4. One multivibrator is controlled by external circuitry so as to be in an unstable condition for the duration of the short period indicated by the pulse P30 of FIG. 4D; and the other is controlled by external circuitry so as to be in an unstable condition for the long period indicated by the pulse P32 of FIG. 4E. The short-period multivibrator is controlled by the connection of a resistor 88 between a terminal (2) and a point of positive operating potential and connecting a resistor 90 and a capacitor 92 in series between the terminal (2) and a point of negative operating potential. The long-period multivibrator, which is actuated by the positive-going edge of the short period multivibrator, is controlled by the connection of a resistor 94 between a terminal (14) and the point of positive operating potential and by connecting a resistor 96 and a capacitor 98 in series between the terminal (14) and the point of negative operating potential. Terminals (11), (13) and (16) are connected to the point of positive operating potential, and terminals (1), (8) and (15) are connected to the point of negative operating potential. Terminals (4) and (6) are connected together, as are terminals (7) and (12). A negative output pulse such as P32 shown in FIG. 4E appears at the connected terminals (3) and (9) and is applied by a lead 100 to terminal (13) of the chip 86 so as to place it in a nonconductive state and cause an output pulse such as shown in FIG. 4F to appear across the output 16, 20 that is proportional to the amplitude of the pace pulse P.

FIG. 4' is a modification of FIG. 4 that provides an independently adjustable response to the pace pulses P by modifying the time constant of the integration circuit to which the pace pulse P is applied. Those components having the same function as in FIG. 4 are designed in the same way and the waveforms of FIGS. 4A through 4C and FIGS. 4D', 4E' and 4F' appear at like-lettered points. A normally nonconductive auxiliary switch $S_A$ and a resistor 102 are connected in series between the input terminal 10, and the output terminal 16. The differentiation circuit 24 and the bipolar comparator 26 of the pace pulse sensing means 22 operate as in FIG. 4 to produce the negative pulses PL and PT of FIG. 4C. The pulse $P_L$ at the leading edge of a pace pulse P triggers a multivibrator 104 so as to cause it to produce the positive pulse P104 shown in FIG. 4D' that is applied so as to close the auxiliary switch $S_A$ and charge the output capacitor 18 with a portion of the pace pulse P through the resistor 102. The duration of the pulse P104 shown in FIG. 4D' and the value of the resistor 102 can be selected to produce a desired voltage across the capacitor 18. The normally closed signal switch $S_s$ is opened at the beginning of the pace pulse P and reclosed following the after-voltage by coupling a multivibrator 106 between it and the output of the bipolar comparator 26. The multivibrator 106 has an output P106 such as indicated in FIG. 4E'.

SECOND SPECIE OF THE INVENTION

Figure 5:
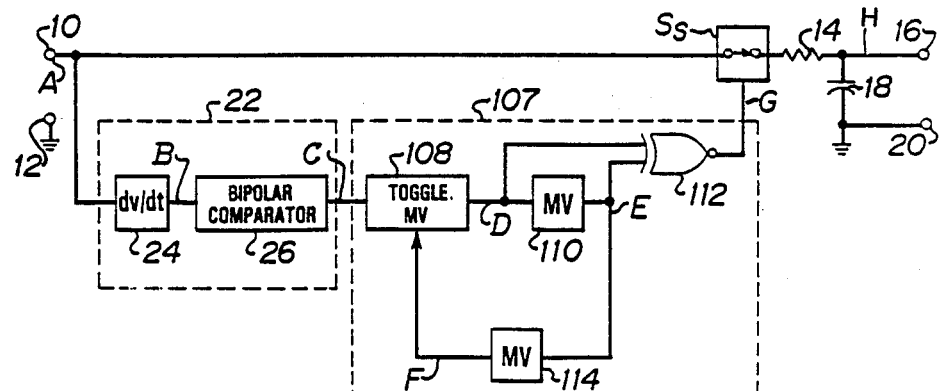
FIG. 5 is a block diagram of a first embodiment of a second specie of an EKG processing circuit of this invention in which the voltage produced in response to pace pulses P is proportional to the product of their amplitude and duration.
Figure 5:
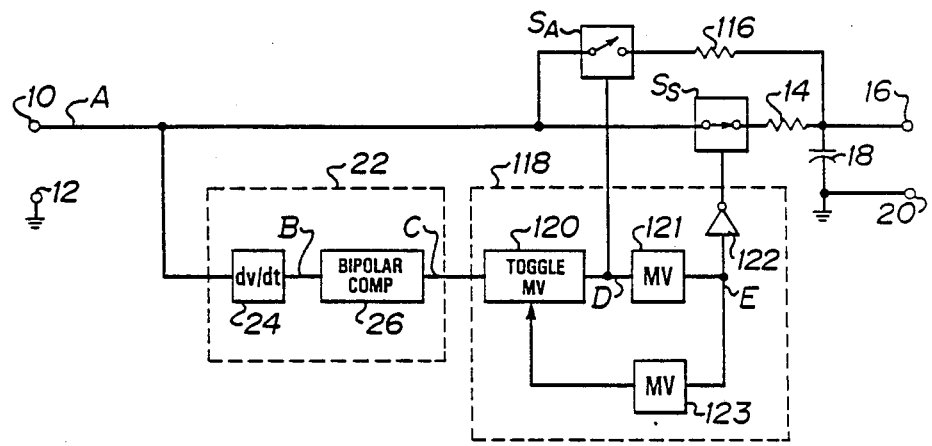

FIG. 5 is a block diagram of a first embodiment of a second specie of the invention in which the substitute pulse PS applied to the output 16, 20 in place of the pace pulse P has an amplitude that is related to the product of the amplitude and duration of the pace pulse P. This is effected by charging the capacitor 18 during the entire pace pulse P rather than during just a part of it. Components corresponding to those in FIG. 4 have the same designations and the waveforms of FIGS. 5A through 5G and the pulse PS of FIG. 5H appear at identically lettered points in FIG. 5.

The pace pulse sensing means 22 is the same as in FIG. 4, but a signal switch control means 107 is provided that differs from the signal switch control means 28 of FIG. 4. The signal switch control means 107 is comprised of a toggle multivibrator 108 that is triggered by the pulses PL and PT supplied by the comparator 26 so as to output a pulse P108 shown in FIG. 5D which is applied to a multivibrator 110 and one input of an EXCLUSIVE NOR gate 112. As shown in FIG. 5E, the multivibrator 110 outputs a pulse P110 that begins at the rising edge of the pulse P108 and lasts until any after-voltage has an insignificant amplitude. The pulse P110 is applied to the other input of the EXCLUSIVE NOR gate 112 so that its output remains high as shown in FIG. 5G until the end of the pace pulse P at which point it becomes low until the end of the pulse P110. When the output of the gate 112 is high, $S_s$ is closed; but when the output of the gate 112 is low, $S_s$ is open. Thus, the signal switch $S_s$ remains closed during the entire pace pulse and is opened immediately thereafter so that the capacitor 18 is charged and is not changed during the after-voltage during the entire pace pulse.

Since the toggle multivibrator 108 could be triggered by a narrow noise spike so as to be in an improper state when a pace pulse P arrives, a very short pulse P114 of about 10 microseconds (shown in FIG. 5F) is developed in response to the termination of the pulse P110 by a monostable multivibrator 114 and applied to a reset input of the toggle multivibrator 108.

FIG. 5' illustrates a second embodiment of the second specie of the invention in which the amplitude of the substitute pulse PS is independently adjustable. Components corresponding to those of FIG. 5 are designated in the same way and the substitute pulses PS' and PS" of FIG. 5H occur at the point H.

The pulse sensing means 22 is the same as in FIG. 5 but a switch control means 118 is different from the switch control means 107 of FIG. 5. The latter is comprised of the toggle multivibrator 120 that is triggered by the pulses PL and PT at the output of the comparator 26 so as to produce a pulse like the pulse P108 shown in FIG. 5D that is positive during the pace pulse P. A normally open auxiliary switch $S_A$ and a resistor 116 are connected in series between the input terminal 10 and the output terminal 16. The pulse at the output of the multivibrator 120 is applied to the auxiliary switch $S_A$ so as to close it during each pace pulse, and to a multivibrator 121 so as to trigger it into an unstable state. The multivibrator 121 outputs a pulse like the pulse P110 of FIG. 5E that is inverted by an inverter 122 and applied to the signal switch $S_s$ so as to place it in a nonconducting state from the leading edge of a pace pulse P until the amplitude of any after-voltage has a negligible value. The multivibrator 123 serves the same purpose as the multivibrator 114 in FIG. 5. By making the value of the resistor 116 less than that of the resistor 14 of FIG. 5, the amplitude of the substitute pulse can be increased from that produced by the circuit of FIG. 5 as indicated at PS' of FIG. 5H; and by making the value of the resistor 116 greater than that of the resistor 14 of FIG. 5, the amplitude of the sustitute pulse can be decreased from that produced by the circuit of FIG. 5 as indicated at PS" of FIG. 5H.

THIRD SPECIE OF THE INVENTION

Figure 6:
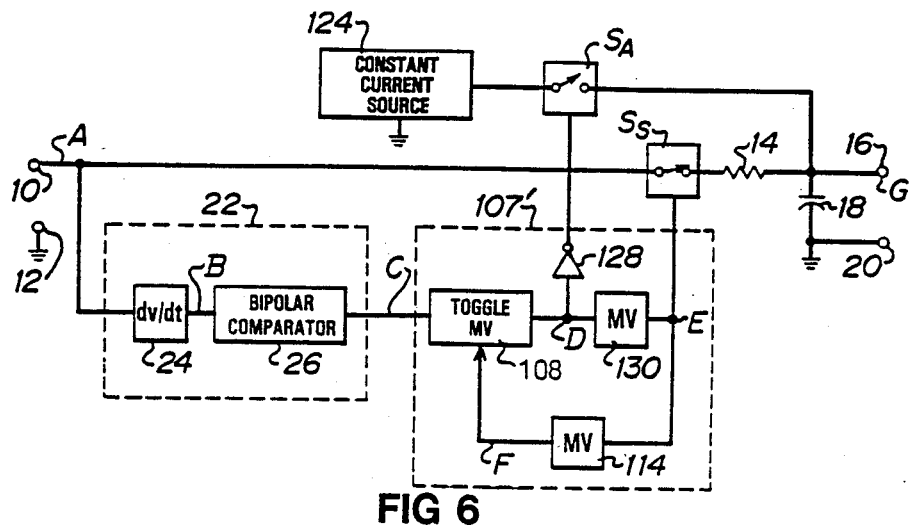
FIG. 6 is a block diagram of a first embodiment of a third specie of an EKG processing circuit of this invention in which the substitute pulse PS is generated by a constant current source and the resulting voltage is related to the pace pulse width.
Figure 6:
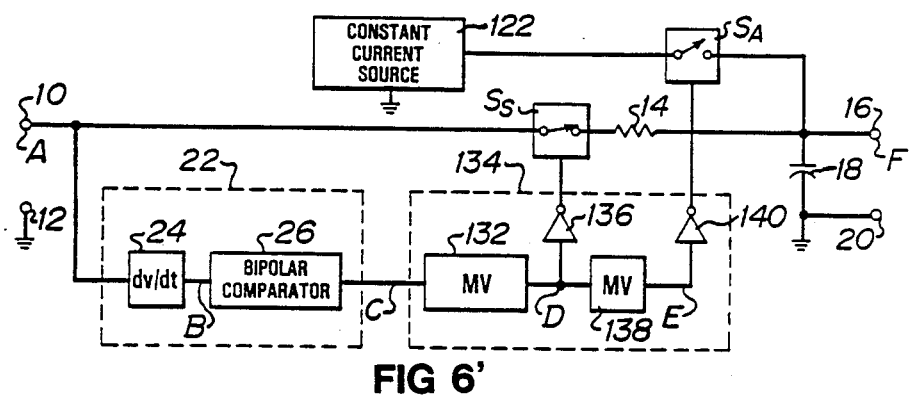

FIG. 6 illustrates a first embodiment of a third specie of the invention in which the substitute pulse PS supplied to the output 16, 20 is generated by charging the output capacitor 18 with a constant current source in such manner that the substitute pulse PS has an amplitude relating only to the width of the pace pulse P. Components corresponding to those in FIG. 5 are designated in the same way and the waveforms of FIGS. 6A through 6G appear at like-lettered points in FIG. 6. A normally nonconducting auxiliary switch $S_A$ is connected so as to place a constant current source 124 in parallel with the capacitor 18 when $S_A$ is closed. As previously explained in connection with FIG. 5, the presence of a pace pulse P at the input 10, 12 causes the bipolar comparator 26 to output pulses PL and PT respectively at the leading and trailing edges of the pace pulse P. The pulse PL is applied to a toggle or bistable multivibrator 108 so as to cause its output to assume a high stable state, and the pulse PT causes the output of the multivibrator 108 to assume a low stable state so as to form the pulse P108 of FIG. 6D that lasts during the entire pace pulse P. The pulse P108 is inverted in an inverter 128 and applied so as to close the normally open auxiliary switch $S_A$ and cause the capacitor 18 to be charged from the constant current source 124 and produce the substitute pulse PS shown in FIG. 6G.

The signal switch $S_s$ is controlled as follows. The leading edge of the pulse P108 causes a monostable multivibrator 130 to output a low state pulse P130 of FIG. 6E that is applied so as to make the normally conductive signal switch $S_s$ nonconductive for a period beginning at the leading edge of the pace pulse P and ending some time after the trailing edge of the pace pulse P when the after-voltage AV has diminished. The multivibrator 114 prevents improper operation in the presence of noise, as explained in connection with FIG. 5.

If it is desired that the substitute pulse PS derived at the output 16, 20 have less amplitude, the auxiliary switch $S_A$ can be made conductive for only the first portion of a pace pulse, by means shown in FIG. 6' in which components corresponding to those of FIG. 6 are designated in the same way and in which the waveforms of FIGS. 6A' through 6F' appear at like-lettered points. In this second embodiment of the third specie of the invention, the pulse PL activates a monostable multivibrator 132 of a means 134 for controlling switches $S_s$ and $S_A$ so as to cause the multivibrator 132 to output a high state pulse P132 of FIG. 6D'. The pulse P132 is inverted by an inverter 136 and applied so as to make the normally conductive signal switch $S_s$ nonconductive during a period beginning at the leading edge of the pace pulse P and ending when the after-voltage AV has diminished sufficiently.

The pulse P132 is also applied so that its leading edge triggers a monostable multivibrator 138 that stays in its unstable condition for less than the duration of a pace pulse P and outputs a pulse P138 of FIG. 6E'. This pulse is applied via an inverter 140 so as to make the normally nonconductive auxiliary switch $S_A$ conductive, thereby causing the capacitor 18 to be charged from the current source 124 and produce the substitute pulse PS shown in FIG. 6F' that lasts until the signal switch $S_s$ is made conductive again at the end of the pulse P132.

Figure 7:
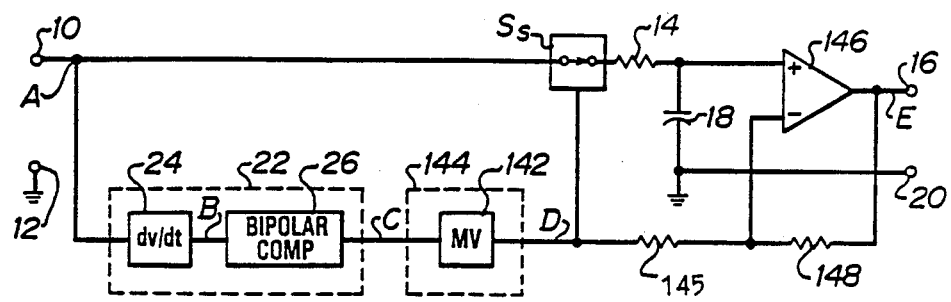
FIG. 7 is a block diagram of a fourth specie of this invention in which the substitute pulse PS is provided by means that does not charge a capacitor.

FIG. 7 is a block diagram of an embodiment of a fourth specie of the invention in which the pulse PS that is substituted for the pace pulse P is not related to any parameter of the pace pulse. Those components that are the same as those of FIG. 1 are designated in the same way, and the waves of FIGS. 7A through 7E appear at like-lettered points in FIG. 7.

As before, a pace pulse P at the input 10, 12 is sensed by means 22 comprised of the differentiation circuit 24 and the bipolar comparator 26 that outpus pulses PL and PT respectively occurring at the leading and trailing edges of the pace pulse P. The pulse PL triggers a monostable multivibrator 142 that is the sole component of a signal switch control means 144 so as to cause it to output a pulse P142 of FIG. 7D. The pulse P142 is applied to the signal switch $S_s$ so as to make it nonconductive.

The pulse P142 is also applied via a resistor 145 to the inverting input of a differential amplifier 146 having a resistor 148 connected between its inverting input and its output. The junction between the resistor 14 and the capacitor 18 is connected to the noninverting input of the amplifier 146.

The operation of FIG. 7 is as follows. The switch control means 144 makes the signal switch $S_s$ nonconductive for a period beginning at the leading edge of a pace pulse P and ending when the after-voltage has little amplitude. The inverting input of the amplifier 146 is negative during the pulse P142 so as to cause a substitute pulse PS, such as shown in FIG. 7E, to appear at the output 16, 20.

Figure 8:
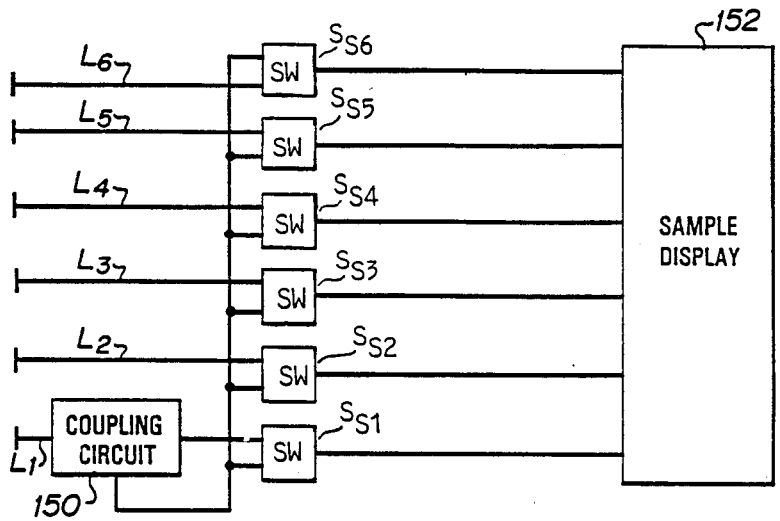
FIG. 8 shows the use of a coupling circuit of this invention in one lead to control the signal switches in its own lead and in a plurality of other leads.

FIG. 8 shows an EKG system having six leads $L_1$ through $L_6$, one of which is connected to a coupling circuit 150 of this invention, and signal switches $S_{s1}$ through $S_{s6}$ that are respectively connected in series with each lead and operated by the signal switch control means of the coupling circuit 150 so as to prevent the after-voltages that may follow the pace pulses on of the leads $L_1$ through $L_6$ from reaching a sample display 152.

What is claimed is:

1. Apparatus for processing EKG signals having pace pulses therein, comprising
    an input having two terminals between which EKG signals and accompanying pace pulses may be applied,
    an output having two terminals between which the processed signals are to appear,
    a normally conductive signal switch and a resistor connected in series between a terminal of said input and a terminal of said output,
    a capacitor direct-current coupled between the terminals of said output, the time constant of said resistor and said capacitor being such as to form a low pass filter passing the highest frequency of interest in said EKG signals and an integration circuit for the pace pulses, and
    means coupled to said input for opening said switch for a given period beginning during a pace pulse and ending at a predetermined time thereafter.

2. Apparatus for processing EKG signals having pace pulses therein, comprising
    an input having two terminals between which EKG signals and accompanying pace pulses may be applied,
    an output having two terminals between which processed EKG signals are to appear,
    a normally closed signal switch,
    a resistor connected in series with said switch between a terminal of said input and a terminal of said output,
    a capacitor direct-current coupled between the terminals of said output, the time constant of said resistor and said capacitor being such as to integrate a pace pulse,
    a differentiator coupled to said input,
    a bipolar comparator coupled to the output of said differentiator,
    means providing a delay of less duration than a pace pulse coupled to the output of said bipolar comparator, a monostable multivibrator coupled to the output of said delay means that, when triggered, stays in the unstable state longer than the duration of a pace pulse, and
    means coupling the output of said monostable multivibrator to said switch so as to make it nonconductive when the multivibrator is in an unstable state.

3. Apparatus for processing EKG signals having pace pulses therein, comprising
    an input having two terminals between which EKG signals and accompanying pace pulses may be applied,
    an output having two terminals between which the processed EKG signals are to appear,
    a capacitor connected between the terminals of said output,
    a normally closed signal switch and a first resistor connected in series between one of said input terminals and one of said output terminals, said first resistor and said capacitor forming a low pass filter that passes only the frequency components of interest in an EKG signal,
    a normally open auxiliary switch and a second resistor connected in series between one of said input terminals and one of said output terminals, the time constant of said capacitor and said second resistor being such as to integrate a pace pulse, a differentiator coupled to said input, a bipolar comparator coupled to the output of said differentiator, a first multivibrator connected between the output of said bipolar comparator and said signal switch so as to open said signal switch at the beginning of a pace pulse and close it at a predetermined time thereafter, and a second multivibrator coupled between the output of said bipolar comparator and said auxiliary switch so as to close it at the beginning of a pace pulse and open it during a pace pulse.

4. Apparatus for processing EKG signals having pace pulses therein, comprising an input having two terminals between which EKG signals and accompanying pace pulses may be applied, an output having two terminals between which the processed EKG signals are to appear, a capacitor connected between the terminals of said output, a switch and a resistor connected in series between said input and said output, said capacitor and said resistor having a time constant such as to integrate a pace pulse, a differentiator coupled to said input, a bipolar comparator coupled to the output of said differentiator, a toggle multivibrator coupled to the output of said bipolar comparator, an EXCLUSIVE NOR gate having one input connected to the output of said multivibrator, a second multivibrator connected between the output of said toggle multivibrator and the other input of the EXCLUSIVE NOR gate, and means coupling the output of said EXCLUSIVE NOR gate to said switch whereby said switch is opened at the end of a pace pulse for a predetermined time.

5. Apparatus for processing EKG signals having pace pulses therein, comprising an input having two terminals between which EKG signals and accompanying pace pulses may be applied, an output having two terminals between which the processed EKG signals are to appear, a capacitor connected between the terminals of said output, a normally closed signal switch and a first resistor connected in series between said input and said output, said capacitor and said first resistor forming a low pass flter that passes only the frequency components of interest in an EKG signal, a normally open auxiliary switch and a second resistor connected in series between said input and said output, the time constant of said capacitor and said second resistor being such as to integrate a pace pulse, a differentiator coupled to said input, a bipolar comparator coupled to the output of said differentiator, a toggle multivibrator coupled to the output of said bipolar comparator, a second multivibrator coupled to the output of said toggle multivibrator, an inverter coupled between the output of said second multivibrator and said signal switch whereby said signal switch is opened at the beginning of a pace pulse and closed a predetermined time thereafter, and a connection between the output of said toggle multivibrator and said auxiliary switch whereby said switch is closed during an entire pace pulse.

6. Apparatus for processing EKG signals having pace pulses therein, comprising an input having two terminals between which EKG signals and pace pulses may be applied, an output having two terminals between which processed signals are to appear, a capacitor connected between the terminals of said output, a normally conductive signal switch connected between one terminal of said input and one terminal of said output, a normally nonconductive auxiliary switch and a source of constant current connected in series across said capacitor, a differentiator coupled to said input, a bipolar comparator coupled to the output of said differentiator, a toggle multivibrator coupled to the output of said bipolar comparator, a second multivibrator coupled to the output of said toggle multivibrator, the output of said second multivibrator being coupled to said signal switch so as to open it from the beginning of a pace pulse until a predetermined time thereafter, and an inverter coupled between the output of said toggle multivibrator and said auxiliary switch whereby so as to close it only during a pace pulse.

7. Apparatus for processing EKG signals having pace pulses therein, comprising an input having two terminals between which EKG signals and pace pulses may be applied, an output having two terminals between which processed signals are to appear, a capacitor connected between the terminals of said output, a normally conductive signal switch connected between one terminal of said input and one terminal of said output, a normally nonconductive auxiliary switch and a source of constant current connected in series across said capacitor, a differentiator coupled to said input, a bipolar comparator coupled to the output of said differentiator, a first multivibrator coupled to the output of said bipolar comparator, an inverter coupled between the output of said first multivibrator and said signal switch so as to open said signal switch from the beginning of a pace pulse until a predetermined time after the pace pulse, a second multivibrator coupled to the output of said first multivibrator, and an inverter coupled between the output of said second multivibrator and said auxiliary switch so as to close said auxiliary switch for a given portion of a pace pulse.

8. Apparatus for processing EKG signals having pace pulses therein, comprising an input having two terminals between which EKG signals and accompanying pace pulses may be applied, an output having two terminals between which processed signals are to appear, a capacitor connected between the terminals of said output, a normally conductive signal switch connected between one terminal of said input and one terminal of said output, a source of constant current and a normally nonconducting auxiliary switch connected in series across said capacitor, means coupled to the terminals of said input for making said signal switch nonconducting during an entire pace pulse and for a period immediately thereafter, and means coupled to the terminals of said input for making said auxiliary switch conductive for at least a portion of a pace pulse.

9. Apparatus for processing EKG waves which may contain pace pulses, comprising an input having a pair of terminals between which an EKG signal may be applied, an output having a pair of terminals between which the processed EKG signal is to appear, a capacitor direct-current-coupled between the terminals of said output, a normally conductive signal switch and resistive means connected in series between one of said input terminals and one of said output terminals, means coupled to the terminals of said input for producing a signal indicating the presence of a pace pulse between the terminals of said input, and signal switch control means responsive to said signal for making said signal switch nonconductive during at least a portion of a pace pulse and for a given time thereafter, the time constant of said resistive means and said capacitor being such as to integrate a pace pulse during the portion of it occurring when the signal switch is conductive.

10. Apparatus as set forth in claim 9 wherein said signal switch control means makes said signal switch nonconductive at a predetermined time after the beginning and before the end of a pace pulse so that the voltage change on said capacitor caused by the charging action occurring during the predetermined time is proportional to the amplitude of the pace pulse.

11. Apparatus as set forth in claim 9 wherein said signal switch control means makes said signal switch nonconductive at the beginning of a pace pulse, a normally nonconductive auxiliary switch and a second resistive means connected in series between said one terminal of said input and said one terminal of said output, and auxiliary switch control means responsive to the signal for making said auxiliary switch conductive during a portion of a pace pulse and the time constant of said second resistive means and said capacitor being different from the time constant of said resistive means and said capacitor and such as to integrate a pace pulse so that the change in voltage across said capacitor caused by the charging action occurring during said portion of a pace pulse is proportional to its amplitude.

12. Apparatus as set forth in claim 9 wherein said signal switch control means makes said signal switch nonconductive at the end of a pace pulse so that the voltage change on said capacitor caused by the charging action occurring during a pace pulse is proportional to the product of the amplitude and duration of the pace pulse.

13. Apparatus as set forth in claim 9 wherein the time constant of said resistive means and said capacitor is such as to form at least part of a low pass filter passing the frequency components of the EKG signal that are of interest, said signal switch control means makes said signal switch nonconductive at the beginning of a pace pulse, a normally nonconductive auxiliary switch and an auxiliary resistor are connected in series between said one terminal of said input and said one terminal of said output, and auxiliary switch control means are provided for making said auxiliary switch conductive only during an entire pace pulse so that the voltage change on said capacitor caused by the charging action occurring during a pace pulse is proportional to the product of the amplitude and duration of the pace pulse.

14. Apparatus as set forth in claim 9 wherein said signal switch control means makes said signal switch nonconductive at the beginning of a pace pulse, a constant current source and a normally nonconductive auxiliary switch are connected in series across said capacitor, and auxiliary switch control means responsive to the signal indicating the presence of a pace pulse for making said auxiliary switch conductive only during an entire pace pulse so that the voltage change on said capacitor caused by the charging action occurring during the pace pulse is proportional to the duration of the pace pulse.

15. Apparatus as set forth in claim 9 wherein said signal switch control means makes said signal switch nonconductive at the beginning of a pace pulse, a constant current source and a normally nonconductive auxiliary switch are connected in series across said capacitor, and auxiliary switch control means responsive to the signal indicating the presence of a pace pulse for making said auxiliary switch conductive only during a part of a pace pulse.

* * * * *

UNITED STATES PATENT AND TRADEMARK OFFICE
CERTIFICATE OF CORRECTION

PATENT NO.  : 4,574,813
DATED       : March 11, 1986
INVENTOR(S) : Richard J. Regan It is certified that error appears in the above-identified patent and that said Letters Patent is hereby corrected as shown below:

| | | |
|---|---|---|
| Column 3 | line 64 | "AV'" should read -- AV -- |
| Column 5 | line 28 | "pas" should read -- pass -- |
| Column 7 | line 3 | "designed" should read -- designated -- |
| | line 60 | after "charged" delete "and is not changed during the" |
| | line 61 | delete "after-voltage"; after "pulse" and before the period (.), insert --- and is not charged during the after-voltage -- |
| Column 8 | line 32 | "sustitute" should read -- substitute -- |

Signed and Sealed this

Nineteenth Day of August 1986

[SEAL]

Attest:

DONALD J. QUIGG

Attesting Officer

Commissioner of Patents and Trademarks